(12) United States Patent
Nokihara et al.

(10) Patent No.: US 8,148,141 B2
(45) Date of Patent: Apr. 3, 2012

(54) PEPTIDE-IMMOBILIZED SUBSTRATE AND METHOD FOR MEASURING TARGET PROTEIN

(75) Inventors: Kiyoshi Nokihara, Kyoto (JP); Hisakazu Mihara, Chigasaki (JP)

(73) Assignee: HiPep Laboratories, Kyoto (JP)

( * ) Notice: Subject to any disclaimer, the term of this patent is extended or adjusted under 35 U.S.C. 154(b) by 676 days.

(21) Appl. No.: 10/476,861

(22) PCT Filed: May 7, 2002

(86) PCT No.: PCT/JP02/04426
§ 371 (c)(1),
(2), (4) Date: Nov. 5, 2004

(87) PCT Pub. No.: WO02/090985
PCT Pub. Date: Nov. 14, 2002

(65) Prior Publication Data
US 2005/0084902 A1    Apr. 21, 2005

(30) Foreign Application Priority Data

May 7, 2001  (JP) ................................. 2001-136606
Jan. 8, 2002  (JP) ..................................... 2002-1759

(51) Int. Cl.
*C12M 1/34* (2006.01)
(52) U.S. Cl. ............... 435/288.7; 435/283.1; 435/287.1; 435/287.2; 435/288.3; 435/7.1; 436/518; 436/524; 436/528
(58) Field of Classification Search .............. 435/283.1, 435/7.1, 287.1, 287.2, 288.3, 288.7; 436/518, 436/524, 528
See application file for complete search history.

(56) References Cited

U.S. PATENT DOCUMENTS

| | | | |
|---|---|---|---|
| 4,507,230 A * | 3/1985 | Tam et al. ...................... | 530/334 |
| 5,591,646 A * | 1/1997 | Hudson et al. .................... | 506/9 |
| 5,998,204 A * | 12/1999 | Tsien et al. .................... | 435/325 |
| 6,197,599 B1 * | 3/2001 | Chin et al. ..................... | 436/518 |
| 6,284,465 B1 * | 9/2001 | Wolber ........................ | 435/6.11 |
| 6,441,152 B1 * | 8/2002 | Johansen et al. ............. | 536/23.1 |
| 6,762,280 B2 * | 7/2004 | Schmidt et al. ............... | 530/300 |

(Continued)

FOREIGN PATENT DOCUMENTS

JP         61-050999 A         3/1986

(Continued)

OTHER PUBLICATIONS

Reineke et al., Current Opinion in Biotechnology, vol. 12, No. 1, pp. 59-64 (Feb. 2001), Applications of peptide arrays prepared by the SPOT technology.
Cotton et al., Chemistry and Biology, vol. 7, No. 4, pp. 253-261 (2000), generation of a dual-labeled fluorescence biosensor for crk-II phosphorylation using solid-phase expresssed protein ligation.

(Continued)

*Primary Examiner* — Melanie J Yu
(74) *Attorney, Agent, or Firm* — Birch, Stewart, Kolasch & Birch, LLP

(57) ABSTRACT

Disclosed is a peptide-immobilized substrate for measuring a target protein, with which the peptide can have a structure required for being recognized by the target protein, with which the accurate loading amount of the peptide can be attained, and by which a trace amount of the target protein may be measured accurately and simply. The peptide-immobilized substrate for measuring a target protein according to the present invention comprises a chemically synthesized peptide having an expected spatial structure or having a binding ability with the target protein, which peptide can bind with the target protein and is immobilized on the substrate.

14 Claims, 2 Drawing Sheets

Library of peptides having spatial structures

Library of peptides having functional factors

Immobilized on chip

U.S. PATENT DOCUMENTS

| | | | |
|---|---|---|---|
| 6,927,025 B1* | 8/2005 | Carr et al. | 435/6 |
| 2002/0004204 A1* | 1/2002 | O'Keefe | 435/6 |
| 2003/0229455 A1* | 12/2003 | Bevilacqua et al. | 702/20 |

FOREIGN PATENT DOCUMENTS

| | | |
|---|---|---|
| JP | 10-25299 A | 1/1998 |
| JP | 2001-503849 A | 3/2001 |
| JP | 2001-242116 A | 9/2001 |
| JP | 2002-017359 A | 1/2002 |
| WO | WO 98/48278 A1 | 10/1998 |
| WO | WO 00/09539 A1 | 2/2000 |
| WO | WO 00/50901 A1 | 8/2000 |
| WO | WO-00/54046 A2 | 9/2000 |

OTHER PUBLICATIONS

Salisbury et al., Journal of the American Chemical Society, vol. 124, No. 50, pp. 14868-14870 (Dec. 2002), Peptide Microarrays for the determination of protease substrate specificity charactrization using fluorescent fingerprint patterns.

Usui et al., Biopolymers (Peptide Science), vol. 76, No. 2, pp. 129-139 (2004), Peptide arrays with Designed secondary structures for Protein.

Takenaka at al., Bio•Kobunshi Symposium Koen Yoshishu $10^{th}$, pp. 21-22 (2000).

Chung, AD Rep, p. 9p (2000).

Sato et al., The Japan Society for Analytical Chemistry Nenkai Koen Yoshishu, vol. 49, pp. 28 (2000).

\* cited by examiner

A, B : fluorescent functional group for labelling

● — : fluorescent functional group for labelling

SEQUENCE LISTING

<160> NUMBER OF SEQ ID NOS: 137

<210> SEQ ID NO 1
<211> LENGTH: 14
<212> TYPE: PRT
<213> ORGANISM: Artificial Sequence
<220> FEATURE:
<223> OTHER INFORMATION: core region of synthetic peptide which binds to calmodulin

<400> SEQUENCE: 1

Leu Lys Lys Leu Leu Lys Leu Leu Lys Lys Leu Leu Lys Leu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: synthetic peptide which binds to calmodulin

<400> SEQUENCE: 2

Cys Glu Leu Lys Lys Leu Leu Lys Leu Leu Lys Lys Leu Leu Lys Leu
1               5                   10                  15

Lys

<210> SEQ ID NO 3
<211> LENGTH: 17
<212> TYPE: PRT
<213> ORGANISM: Artificial Sequence
<220> FEATURE:
<223> OTHER INFORMATION: synthetic peptide which binds to calmodulin

<400> SEQUENCE: 3

Glu Leu Lys Lys Leu Leu Lys Leu Leu Lys Lys Leu Leu Lys Leu Lys
1               5                   10                  15

Cys

<210> SEQ ID NO 4
<211> LENGTH: 16
<212> TYPE: PRT
<213> ORGANISM: Artificial Sequence
<220> FEATURE:
<223> OTHER INFORMATION: synthetic peptide which binds to calmodulin

<400> SEQUENCE: 4

Lys Leu Lys Lys Leu Leu Lys Leu Leu Lys Lys Leu Leu Lys Leu Cys
1               5                   10                  15

<210> SEQ ID NO 5
<211> LENGTH: 9
<212> TYPE: PRT
<213> ORGANISM: Artificial Sequence
<220> FEATURE:
<223> OTHER INFORMATION: core region of synthetic peptide which binds to amylase

<400> SEQUENCE: 5

Tyr Gln Ser Trp Arg Tyr Ser Gln Ala

```
<210> SEQ ID NO 6
<211> LENGTH: 11
<212> TYPE: PRT
<213> ORGANISM: Artificial Sequence
<220> FEATURE:
<223> OTHER INFORMATION: synthetic peptide which binds to amylase

<400> SEQUENCE: 6

Lys Tyr Gln Ser Trp Arg Tyr Ser Gln Ala Cys
1               5                   10

<210> SEQ ID NO 7
<211> LENGTH: 15
<212> TYPE: PRT
<213> ORGANISM: Artificial Sequence
<220> FEATURE:
<223> OTHER INFORMATION: synthetic peptide used in fingerprint method in
      Example 3
<220> FEATURE:
<221> NAME/KEY: misc_feature
<222> LOCATION: (7)..(10)
<223> OTHER INFORMATION: Xaa can be any naturally occurring amino acid,
      most preferably selected from SEQ ID NOS: 8-133

<400> SEQUENCE: 7

Cys Glu Thr Ile Thr Val Xaa Xaa Xaa Xaa Lys Thr Tyr Lys Lys
1               5                   10                  15

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 8

Leu His Gly Glu
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 9

Leu Pro Gly Glu
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 10

Arg Pro His Glu
1

<210> SEQ ID NO 11
<211> LENGTH: 4
<212> TYPE: PRT
```

```
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 11

Tyr Gly Leu Glu
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 12

Trp Arg Leu Glu
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 13

Trp Tyr Leu Glu
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 14

His Gly Pro Glu
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 15

Leu His Pro Glu
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 16

His Ser Pro Glu
1
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 17

Tyr Ser Pro Glu
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 18

Tyr Trp Pro Glu
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 19

Leu Tyr Pro Glu
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 20

Leu Gly Ser Glu
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 21

Trp His Ser Glu
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 22
```

Tyr His Ser Glu
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 23

Pro Trp Ser Glu
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 24

Pro His Trp Glu
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 25

Gly Pro Trp Glu
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 26

Pro Gly Tyr Glu
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 27

Arg Pro Tyr Glu
1

<210> SEQ ID NO 28
<211> LENGTH: 4
<212> TYPE: PRT
<213> ORGANISM: Artificial Sequence
<220> FEATURE:

-continued

<223> OTHER INFORMATION: Description of Artificial Sequence: Peptide
      fragment of SEQ ID NO: 7 and example 3

<400> SEQUENCE: 28

Ser His Glu Gly
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 29

Pro Arg Glu Gly
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 30

Trp Ser Glu Gly
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 31

Ser Pro His Gly
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 32

Trp Ser His Gly
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 33

Tyr Ser Leu Gly
1

<210> SEQ ID NO 34

```
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 34

Trp His Pro Gly
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 35

Tyr His Pro Gly
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 36

Trp Arg Pro Gly
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 37

Leu Ser Pro Gly
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 38

Arg Tyr Pro Gly
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 39

Leu Glu Arg Gly
```

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Peptide fragment of SEQ ID NO: 7 and example 3

<400> SEQUENCE: 40

Tyr His Arg Gly
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Peptide fragment of SEQ ID NO: 7 and example 3

<400> SEQUENCE: 41

Arg His Trp Gly
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Peptide fragment of SEQ ID NO: 7 and example 3

<400> SEQUENCE: 42

Ser Tyr Trp Gly
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Peptide fragment of SEQ ID NO: 7 and example 3

<400> SEQUENCE: 43

Trp Glu Tyr Gly
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Peptide fragment of SEQ ID NO: 7 and example 3

<400> SEQUENCE: 44

Glu His Tyr Gly
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Peptide fragment of SEQ ID NO: 7 and example 3

<400> SEQUENCE: 45

Glu Arg Tyr Gly
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 46

Leu Arg Tyr Gly
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 47

Glu Ser Tyr Gly
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 48

Arg Gly Glu His
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 49

Leu Tyr Glu His
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 50

Trp Arg Leu His
1

<210> SEQ ID NO 51
<211> LENGTH: 4
<212> TYPE: PRT

```
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 51

Gly Trp Leu His
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 52

Gly Arg Pro His
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 53

Arg Ser Pro His
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 54

Leu Trp Pro His
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 55

Leu Ser Arg His
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 56

Leu Trp Ser His
1
```

```
<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 57

Leu Tyr Ser His
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 58

Gly Glu Trp His
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 59

Ser Gly Tyr His
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 60

Arg Tyr Glu Leu
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 61

Trp Pro Gly Leu
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 62
```

Ser Gly His Leu
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 63

His Ser Pro Leu
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 64

Glu His Arg Leu
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 65

His Glu Ser Leu
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 66

Tyr Pro Ser Leu
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 67

Arg Trp Ser Leu
1

<210> SEQ ID NO 68
<211> LENGTH: 4
<212> TYPE: PRT
<213> ORGANISM: Artificial Sequence
<220> FEATURE:

<223> OTHER INFORMATION: Description of Artificial Sequence: Peptide
      fragment of SEQ ID NO: 7 and example 3

<400> SEQUENCE: 68

Pro Glu Trp Leu
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 69

Pro Arg Trp Leu
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 70

Gly His Tyr Leu
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 71

Arg Trp Tyr Leu
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 72

Tyr Trp Gly Pro
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 73

Tyr Leu His Pro
1

<210> SEQ ID NO 74

```
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 74

Leu Arg His Pro
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 75

His Gly Leu Pro
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 76

Leu Glu Arg Pro
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 77

Gly Leu Arg Pro
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 78

Leu Tyr Arg Pro
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 79

Gly Glu Ser Pro
```

```
<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 80

Glu Leu Ser Pro
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 81

Glu Arg Ser Pro
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 82

Leu Arg Ser Pro
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 83

Gly Leu Tyr Pro
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 84

Ser Trp Tyr Pro
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3
```

-continued

<400> SEQUENCE: 85

Pro Trp Glu Arg
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 86

Trp Glu Gly Arg
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 87

His Leu Gly Arg
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 88

Tyr His Leu Arg
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 89

Ser Gly Pro Arg
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 90

Trp His Pro Arg
1

<210> SEQ ID NO 91
<211> LENGTH: 4
<212> TYPE: PRT

```
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 91

Trp Ser Pro Arg
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 92

Trp Glu Ser Arg
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 93

His Trp Ser Arg
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 94

Ser Pro Tyr Arg
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 95

Gly Trp Tyr Arg
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 96

Gly Arg Glu Ser
1
```

```
<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 97

Pro Trp Gly Ser
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 98

Pro Tyr Gly Ser
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 99

Arg Gly His Ser
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 100

Trp Pro Leu Ser
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 101

Glu Arg Leu Ser
1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 102
```

Glu Tyr Leu Ser
1

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 103

Glu His Arg Ser
1

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 104

Gly Leu Arg Ser
1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 105

Gly Trp Arg Ser
1

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 106

Arg Glu Tyr Ser
1

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 107

Arg Leu Tyr Ser
1

<210> SEQ ID NO 108
<211> LENGTH: 4
<212> TYPE: PRT
<213> ORGANISM: Artificial Sequence
<220> FEATURE:

-continued

<223> OTHER INFORMATION: Description of Artificial Sequence: Peptide
      fragment of SEQ ID NO: 7 and example 3

<400> SEQUENCE: 108

Gly Arg Tyr Ser
1

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 109

His Trp Tyr Ser
1

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 110

Gly Leu Glu Trp
1

<210> SEQ ID NO 111
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 111

Tyr His Gly Trp
1

<210> SEQ ID NO 112
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 112

Arg Leu Gly Trp
1

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 113

Ser Leu Gly Trp
1

<210> SEQ ID NO 114

```
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 114

Leu Glu His Trp
1

<210> SEQ ID NO 115
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 115

Tyr Arg His Trp
1

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 116

Pro Ser His Trp
1

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 117

Glu Tyr His Trp
1

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 118

Tyr Gly Leu Trp
1

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 119

Glu His Arg Trp
```

```
<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 120

Pro Tyr Arg Trp
1

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 121

Leu Glu Ser Trp
1

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 122

Glu Tyr Ser Trp
1

<210> SEQ ID NO 123
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 123

His Pro Tyr Trp
1

<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3

<400> SEQUENCE: 124

Arg His Glu Tyr
1

<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence: Peptide
      fragment of SEQ ID NO: 7 and example 3
```

```
<400> SEQUENCE: 125

His Pro Glu Tyr
1

<210> SEQ ID NO 126
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 126

Trp Leu His Tyr
1

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 127

Arg Pro His Tyr
1

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 128

Ser Pro His Tyr
1

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 129

Ser Arg His Tyr
1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 130

Trp Ser Leu Tyr
1

<210> SEQ ID NO 131
<211> LENGTH: 4
<212> TYPE: PRT
```

```
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 131

Pro Trp Leu Tyr
1

<210> SEQ ID NO 132
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 132

Trp Glu Arg Tyr
1

<210> SEQ ID NO 133
<211> LENGTH: 4
<212> TYPE: PRT
<213> ORGANISM: Artificial Sequence
<220> FEATURE:
<223> OTHER INFORMATION: Description of Artificial Sequence:  Peptide
      fragment of SEQ ID NO: 7 and example 3

<400> SEQUENCE: 133

Arg Ser Trp Tyr
1

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr Gln Ser Trp Arg Tyr Ser Gln Ala Cys
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Gln Ser Trp Arg Tyr Ser Gln Ala Lys
1               5                   10

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Glu Thr Ile Thr Val Ser Trp Arg Tyr Lys Thr Tyr Lys Lys
1               5                   10                  15
```

```
<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Trp Arg Tyr
```

PEPTIDE-IMMOBILIZED SUBSTRATE AND METHOD FOR MEASURING TARGET PROTEIN

This application is the national phase under 35 U.S.C. §371 of PCT International Application No. PCT/JP02/04426 which has an International filing date of May 7, 2002, which designated the United States of America.

TECHNICAL FIELD

The present invention relates to a peptide-immobilized substrate for measuring (a) target protein(s), and to a method for measuring the target protein(s) using the same.

BACKGROUND ART

Analyses of functions of proteins existing in the body are important tasks. Methods for identifying and quantifying these expressed proteins satisfy the wide social demands from the clarification of cell functions in the research field to the diagnoses and therapies in the medical field. As means for identifying and quantifying proteins, methods utilizing antibodies and various biosensor systems utilizing arrays of specific proteins are known.

The concept for developing the conventional protein chips is based on immobilization of proteins or fragments thereof, whose structures are known. Immobilization of antibody molecules is also based on this concept. By this method, quantification of the loading amount is problematic, and uniform immobilization is difficult. Particularly, since the yield of immobilization (loading amount) is generally low and depends on the properties of the peptide fragments, the method lacks reliability and so wide use thereof is prevented. Further, in cases where protein fragments are used, the sites of cleavage are restricted because of specificities of the cleavage (if the proteins are cleaved without specificities, the resultants are random fragments and so the molecules immobilized on the chips cannot be identified), thus, free design can not be accomplished. Still further, the thus immobilized proteins have structures different from those in the body, and may not have the structures indispensable for attaining the desired recognitions. These are problems in practice.

Methods for analyzing interactions between peptides and proteins in solutions using fluorometer or the like are known. However, with these methods, considerable amount of samples are necessary, so that a long time is required for sample preparation. Recently, methods such as surface plasmon or the like are used. However, the apparatuses are expensive, the sensitivities are generally low, and simple measurements at local places cannot be attained. Thus, by the conventional methods, treatments of numerous samples are difficult.

DISCLOSURE OF THE INVENTION

An object of the present invention is to provide a peptide-immobilized substrate for measuring (a) target protein(s), with which the peptide can have a structure required for being recognized by the target protein, with which the accurate loading amount of the peptide can be attained, and by which (a) trace amount(s) of the target protein(s) may be measured accurately and simply.

The present inventors intensively studied to discover that the above-described object may be attained by a peptide-immobilized substrate for measuring a target protein, comprising a chemically synthesized peptide having an expected spatial structures or having a binding ability with the target protein, which the peptide can bind with the target proteins and which is immobilized on the substrate, thereby completing the present invention. Further, the present inventors inferred that a protein in a test sample may be easily and simply measured, or a protein contained in an unknown test sample may be identified or characterized by immobilizing a plurality of chemically synthesized peptides on a substrate; reacting the peptides with a test sample which may contain the target protein; assigning a visible physical value to the signal measured for each of the peptides; and outputting visible data of the peptides in an array.

That is, the present invention provides a peptide-immobilized substrate for measuring (a) target protein(s), comprising (a) chemically synthesized peptide(s) having (an) expected spatial structure(s) or having (a) binding ability(abilities) with said target protein(s), which peptide(s) can bind with said target protein(s) and which is(are) immobilized on said substrate. The present invention also provides a method for measuring (a) target protein(s) comprising contacting said peptide-immobilized substrate according to the present invention with said target protein(s); and measuring said target protein(s) bound to said peptide(s) based on the change of said signal(s). The present invention further provides a method for measuring (a) protein(s) in a test sample, comprising the steps of bringing a plurality of chemically synthesized peptides each of which has an expected spatial structure or a binding ability with the target protein, which can or might bind to the target protein, into contact with said test sample which may contain the target protein(s), said plurality of peptides being immobilized on the same or different substrates; measuring the signals which change upon binding between the peptides and the target protein(s); converting each of the values measured for each peptide into data with which differences between measured values may be recognized with naked eye and outputting visible data of the peptides in an array. The present invention still further provides a method for identifying or characterizing (a) protein(s) in a test sample comprising carrying out the method according to the present invention for various test samples; accumulating outputted measured values to produce a database; comparing measured data for an unknown test sample with the measured data in said database thereby identifying or characterizing said unknown test sample.

By the present invention, a novel peptide-immobilized substrate for measuring a target protein, by which a trace amount of target protein may be measured accurately and simply, was provided. In the peptide-immobilized substrate according to the present invention, each of the peptides is a chemically synthesized peptide, and may be immobilized on the substrate under the conditions wherein the functional groups in the side chains of the amino acids are protected or unprotected. That is, the peptide may be immobilized on the substrate at a particular site, and the effective immobilizing amount may be arbitrarily controlled. Further, the peptide may be freely designed, so that an arbitrary label or functional molecular group may be attached to an arbitrary site, or a peptide containing an amino acid which does not occur in natural proteins may be employed. Still further, by the fingerprint method according to the present invention, identification or characterization of the protein contained in the test sample may be attained easily and quickly, and a number of test samples or unknown test samples may be measured.

BEST MODE FOR CARRYING OUT THE INVENTION

Figure 1:
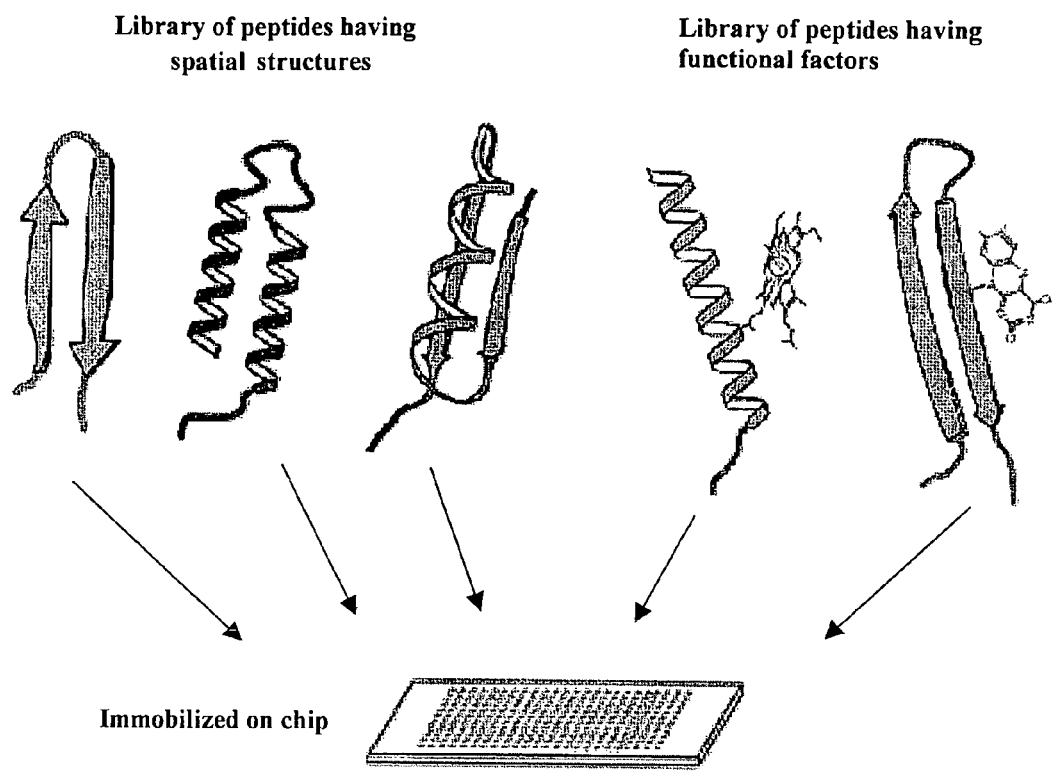
FIG. 1 schematically shows the concept of the peptide-immobilized substrate according to the present invention.

In the present invention, the peptide to be immobilized on the substrate is a chemically synthesized peptide. Most of the naturally occurring proteins have the properties to molecularly recognize the oligopeptides having particular spatial structures and bind with them (Reference: W. E. Stites, Chem Rev, 97, 1233-1250 (1997), Protein-protein interactions: Interface structure, binding thermodynamics, and mutational analysis; D. P. Fairlie et al, Curr. Medicinal Chem., 5, 29-62 (1998) Toward protein surface mimetics; and A. G. Cochran, Chem & Biol, 7, R85-R94 (2000), Antagonist of protein-protein interactions). It is predetermined what protein binds with what oligopeptide having what spatial structure. The first candidate of the peptide used in the present invention is such a peptide having a particular spatial structure. The spatial structures of the oligopeptide, which bind with proteins include various spatial structures such as α-helix, α-loop-α, β-turn, β-loop-β and β-strand. As the peptide to be immobilized on the substrate, peptides having such a particular spatial structure are exemplified. These spatial structures are those which the peptide may have when the peptide is bound with the target protein, and the peptide does not necessarily have these spatial structures when it is merely immobilized on the substrate. In the present invention, the term "having an expected spatial structure" means that the peptide has the expected spatial structure when bound with the target protein. It should be noted that the entire peptide does not necessarily has the expected spatial structure, as long as most part of the peptide (preferably not less than 60%, more preferably not less than 70% in terms of the number of amino acids) has the expected spatial structure. Therefore, to one or both terminal regions of the peptide, the label(s) hereinbelow described may be bound, and the region(s) may not participate in the formation of the expected spatial structure. It is preferred rather to separate the region(s) (hereinafter also referred to as "binding region") at which the peptide is immobilized on the substrate or to which the label(s) is(are) attached and the region to be subjected to the binding with the target protein. It is preferred here that the region (hereinafter also referred to as "core region") to be subjected to the binding with the target protein have the spatial structure which is optimum to the binding. In this case, the binding region(s) is(are) preferably attached to one or both termini of the core region. The peptide having the above-mentioned spatial structure may have a circular structure. In some cases, by making the peptide in a circular form, the binding affinity with the protein may be largely increased. Although a peptide antigen may be chemically synthesized and may be used as the peptide for measuring an antibody, the binding between the peptide and the target protein is not necessarily antigen-antibody reaction at all.

As the proteins which bind with the oligopeptides having the above-described spatial structures, the following proteins are exemplified. As the proteins which bind with an oligopeptide having α-helix structure, calmodulin and gp41 of HIV are exemplified. As the proteins which bind with an oligopeptide having β-loop structure, amylase is exemplified. As the proteins which bind with a β-strand peptide, MHC proteins, aspartic acid proteases, HIV-1 protease, cysteine proteases, metalloproteases and serine proteases are exemplified. As the proteins which bind with a β-loop-β or β-turn peptide, fibronectin, LH-RH receptors, substance P receptors, somatostatin receptors and the like are exemplified. But the proteins are not restricted thereto.

In addition to the above-described peptides having the expected spatial structures, peptide derivatives having binding abilities with the target proteins, such as those in which an organic molecule group (functional molecule group) known to have an interaction with a protein is attached to a particular site, may also be used as the peptide. Examples of such functional molecule groups include porphyrin derivatives (heme), flavin derivatives, alkyl groups such as retinal and palmityl group, nucleic acid bases and peptide nucleic acids, but the functional molecule groups are not restricted thereto.

As the proteins which bind with these functional molecule groups, the following proteins are exemplified. As the proteins which bind with porphyrin derivative (heme)-containing peptides, apo-heme proteins are exemplified. As the proteins which bind with flavin derivative-containing peptides, apo-flavin proteins are exemplified. As the proteins which bind with peptides containing alkyl groups such as retinal and palmityl group, lipocalin proteins are exemplified. As the proteins which bind with the nucleic acid base-containing peptides, DNases, RNases, various gene function-controlling proteins and RNA-binding proteins are exemplified.

The concept of the peptide-immobilized substrate comprising a chemically synthesized peptide having an expected spatial structure or having a binding ability with the target protein, which peptide is immobilized on the substrate, is schematically shown in FIG. 1.

With the technology at present, what amino acid sequence is necessary for attaining a particular spatial structure may be easily determined by using a computer. Computer softwares for carrying out such a molecular designing are commercially available, and the sequence of the peptide having the expected spatial structure may easily be determined by using the computer softwares. The size of the peptide is not restricted, and usually, the number of amino acids is preferably about 2 to 50, more preferably about 5 to 20.

The target protein bound with the peptide immobilized on the substrate may be measured by various methods. Examples of these methods include the methods in which the peptide to be immobilized is labeled with (a) label(s) whose signal changes upon binding of the peptide with the target protein, and the target protein is measured based on the change of the label(s); surface plasmon resonance method; Grating method which is a modification of surface plasmon that does not use a prism; and mass-spectrometric analyses, but the methods are not restricted thereto. Among these, the methods in which the peptide to be immobilized is labeled with (a) label(s) whose signal changes upon binding of the peptide with the target protein are preferred because they have the highest sensitivities and reproducibilities.

As mentioned above, the peptide used in the present invention is preferably labeled with (a) label(s) which changes the signal upon binding of the peptide with the target protein. Examples of such a label include fluorescent labels, spin labels, UV or visible light-absorbing dyes, radioisotopes, stable isotopes and enzymes which cause chemiluminescent reactions (alkaline phosphatase, acid phosphatase, luciferase, green fluorescence protein and the like), but the labels are not restricted thereto. Among these, fluorescent labels are most preferred. Examples of fluorescent labels include fluorescein and derivatives thereof having the fluorescein structure such as carboxyfluorescein; dansyl group and derivatives thereof having the structure of dansyl group such as ethyldansyl group; coumarin derivatives; pyrene derivatives; and naphthalene derivatives, but the fluorescent labels are not restricted thereto. These fluorescent label reagents per se are known and many of them are commercially available. Further, the methods per se for labeling an amino acid by binding a commercially available fluorescent dye with (a) functional group(s) in the amino acid, such as amino group, are known. For example, the label may easily be introduced by binding the label to the side chain of lysine, glutamic acid or cysteine, or to the amino terminal or carboxyl terminal of the peptide, by the method described in Example 1. Since various fluorescence-labeled building blocks used for the synthesis are commercially available from Molecular Probe, U.S. and so on, these commercially available building blocks may be used as they are.

As preferred examples of the fluorescent labels, chemical structures of tetramethylrhodamine and carboxyfluorescein are shown in Formulae [I] and [II] below, respectively.

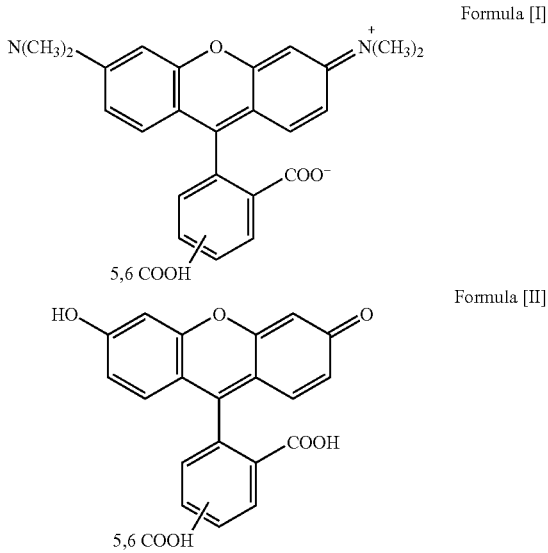

The signals emitted by the above-described labels are changed upon binding of the peptide with the target protein. Although the signal is changed even in cases where a single label is bound to the peptide, it is preferred to bind a plurality of different labels to different sites in the peptide because the change of the signals may be detected more sensitively and so the detection sensitivity may be further promoted. In the especially preferred mode, two types of fluorescent pigments whose fluorescent wavelengths are different are bound to different sites in the peptide. By so doing, sensitive detection may be attained utilizing fluorescence resonance energy transfer (FRET) system. Examples of the combinations of the fluorescent labels, which are preferred for attaining FRET, include combinations of a fluorescein derivative and a rhodamine derivative; a dansyl derivative and a fluorescein derivative; and a pyrene derivative and a fluorescein derivative, but the combinations are not restricted thereto. Examples of the combinations of the fluorescent labels, which are preferred for fluorescent-quenching system utilizing the same mechanism as FRET, include combinations of a dansyl derivative and dabsyl derivative; and a pyrene derivative and a nitrobenzene derivative, but the combinations are not restricted thereto.

The site(s) at which the label(s) is(are) bound is(are) preferably one or both termini of the peptide. It is preferred to bind different labels, preferably two types of fluorescent labels whose fluorescent wavelengths are different, to the both end regions of the peptide.

It is also preferred to employ a peptide whose one end is cysteine for binding the peptide to the substrate.

Figure 2:
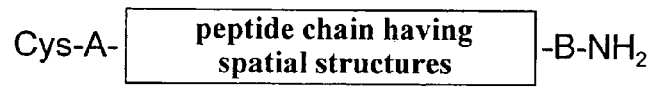
FIG. 2 schematically shows a linear structure of the peptide used in the present invention.
Figure 2:
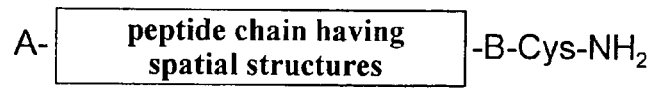

Thus, as examples of preferred peptides, those having the structures shown in FIG. 2 are exemplified. In FIG. 2, A and B denote amino acid residues whose side chains are bound with the fluorescent labels. In these cases, each of the peptide chains is bound to the substrate through the sulfhydryl group in the side chain of the Cys residue.

Among the peptides represented by FIG. 2, preferred examples are those wherein B is Lys residue whose ε-position is bound with tetramethylrhodamine, and A is Lys residue whose ε-position is bound with fluorescein. By employing such a structure, the peptide is a labeled peptide having two types of different fluorescent groups at both termini, and measurement utilizing FRET may be attained. It should be noted that the amino acid residues A and B are not restricted to Lys, but any compounds having functional groups which are relatively highly reactive, such as Orn (ornithine), Glu (glutamic acid) and cysteine may be employed. By introducing groups for labeling utilizing the highly reactive functional groups, building blocks may be prepared. In cases where similar reactive functional groups in side chains do not exist in the peptide having the expected spatial structure, the label groups may be introduced site-specifically, after synthesis of the peptide (assembly of amino acid residues). These synthesis procedures are well-known in the field of peptide synthesis chemistry. One of the functional groups in each combination shown in Table 1 below may be employed, and so the amino acid is not restricted to Cys. Thus, if similar reactive functional groups in the side chains do not exist in the peptide having the expected spatial structure, the peptide may be immobilized site-specifically. The residue such as Cys used for immobilization may be arranged after the C-terminal (after B in the above-mentioned drawing). That is, among the two structures shown in FIG. 2, the structure shown in the lower location may be employed. In FIG. 2, the portion indicated as "peptide chain having the expected spatial structure" is the core region mentioned above.

The peptides used in the present invention are those chemically synthesized. By using a chemically synthesized peptide, the peptide may be synthesized while protecting the functional groups in the side chains of the amino acids, and the synthesized peptide may be bound to the substrate site-specifically. In cases where the peptide to be immobilized is a protected peptide, it is deprotected after immobilization of the peptide. It is also possible to immobilize a free (unprotected) peptide. For example, by arranging Cys residue at the terminal, or by arranging one of avidin and biotin, site-specific binding may be easily attained even if the peptide is unprotected (see Table 1 below). By this, the peptide may be bound to the substrate at a prescribed site, and the loading amount of the effective peptide (i.e., the peptide which can have the expected spatial structure) may be arbitrarily controlled. The protected functional groups are usually deprotected after the peptide is bound to the substrate. Thus, binding of the peptide to the substrate at a site with which the expected spatial structure cannot be attained when it encounters the protein which interacts with the peptide can surely be prevented. Further, by chemically synthesizing the peptide, the peptide may easily be purified and assayed, so that the loading amount to the substrate may surely be controlled. Still further, the above-described functional molecule groups or the labels may easily be introduced to the amino acids, and in turn, may easily be bound to the peptide. Still further, in cases where it is preferred to use an amino acid which does not naturally occur, such an amino acid may easily be incorporated into the peptide. Thus, the peptides in which all or a part of the amino acid residues constituting the peptide chain are D-amino acids which are not naturally occurring, and the peptides having functional groups other than amino acids, such as heme, flavin and alkyl chains, and the like may also be employed as the peptide to be immobilized, so that the flexibility of measurement is largely increased.

The chemical synthesis per se of the peptide may be carried out by well-known methods, and may easily be carried out by using a commercially available peptide synthesizer. In this case, it is preferred to carry out the synthesis while protecting the functional groups of the amino acids. The methods per se for protecting the functional groups in the side chains of amino acids are well-known and described in, for example, Kiyoshi NOKIHARA, Journal of Synthetic Organic Chemistry Japan, 52, 347-358, 1994, "Highly Efficient Peptide Synthesis: Simultaneous and Automatic Synthesis of Multiple Peptides and Peptide Library"; Kiyoshi NOKIHARA and Yoshio YOKOMIZO, Shimadzu Review, 52, 1-8, 1995, "Cleaving Off of Synthetic Peptides by Fmoc-tBu Strategy"; Kiyoshi NOKIHARA, Shimadzu Review, 50, 13-24, 1993, "Reagents for Highly Efficient Solid Phase Synthesis of Peptides"; Kiyoshi NOKIHARA, Shimadzu Review, 50, 3-12, 1993, "Fundamental of Peptide Chemical Synthesis"; Kiyoshi NOKIHARA, Rintaro YAMAMOTO, Hajime HAZAMA, Shin NAKAMURA, Shimadzu Review, 50, 33-43, 1993 "Development of Practical Simultaneous Multiple Solid Phase Peptide Synthesizer PSSM-8"; and K. Nokihara, R. Yamamoto, M. Hazama, O. Wakizawa, S. Nakamura, and M. Yamaguchi, Peptide Chemistry 1991, ed., A. Suzuki, Protein Research Foundation, Osaka, 203-208, 1992, "Development and Applications of a Novel and Practical Simultaneous Multiple Solid Phase Peptide Synthesizer"; Chan, W. C.; White, P. D. Fmoc Solid Phase Peptide Synthesis: A Practical Approach; Oxford University Press: New York, 2000; pp 41-76.

The chemically synthesized peptide is then immobilized on the substrate. This may preferably be attained by reacting the amino group, carboxyl group or the like of the peptide with the amino group, carboxyl group or the like on the substrate thereby binding the peptide to the substrate by covalent bond. Alternatively, biotin or avidin is bound to the peptide (this may be carried out through the functional group in the side chain of a desired amino acid by a conventional method), and the biotin or avidin may be bound to the avidin or biotin fixed on the substrate. Examples of the combination of the functional group (or substance) and the functional group (or substance) on the peptide are shown in Table 1. The methods per se for immobilizing the peptide on the substrate through the reaction between the functional groups (or substances) shown in Table 1 are well-known. The methods for preparing the substrate having the functional groups (or substances) shown in Table 1 are also well-known, and such substrates are commercially available. The commercially available substrates may preferably be employed.

TABLE 1

| Substrate | Peptide | Reagent for Immobilization |
| --- | --- | --- |
| Amino group | Amino group | Glutaraldehyde |
| Amino group | Carboxyl group | Carbodiimide |
| Carboxyl group | Amino group | Carbodiimide |

TABLE 1-continued

| Substrate | Peptide | Reagent for Immobilization |
| --- | --- | --- |
| Sulfhydryl group | Bromoacetyl group | Spontaneously reacts upon mixing. |
| Bromoacetyl group | Sulfhydryl group | Spontaneously reacts upon mixing. |
| Biotin | Avidin | Spontaneously reacts upon mixing. |
| Avidin | Biotin | Spontaneously reacts upon mixing. |
| Sulfhydryl group | Sulfhydryl group | Oxidation (under alkaline pH) |
| Aldehyde group | Amino group | Spontaneously reacts upon mixing. |
| Amino group | Aldehyde group | Spontaneously reacts upon mixing. |
| Aldehyde group | Hydroxylamino group | Spontaneously reacts upon mixing. |
| Hydroxyamino group | Aldehyde group | Spontaneously reacts upon mixing. |
| Aldehyde group | Hydrazino group | Spontaneously reacts upon mixing. |
| Hydrazino group | Aldehyde group | Spontaneously reacts upon mixing. |
| Aldehyde group | Sulfhydryl group | Spontaneously reacts upon mixing. |
| Sulfhydryl group | Aldehyde group | Spontaneously reacts upon mixing. |
| Active ester group | Amino group | Spontaneously reacts upon mixing. |
| Amino group | Active ester group | Spontaneously reacts upon mixing. |

The amount of each peptide to be immobilized on the substrate is not restricted at all, and may be appropriately selected depending on the concentration of the target protein in the test sample, reactivity between the peptide and the target protein and the like. For example, it is about 1 fmol (1 femto mol) to 1000 nmol, preferably about 0.01 pmol to 1000 pmol.

The binding of the peptide to the substrate may also be carried out by physical adsorption. In this case, the immobilization of the peptide may be attained by contacting a solution of the peptide in a buffer with the substrate. In this case, the immobilization reaction may be carried out, for example, at room temperature for about 15 minutes to 2 hours, or at 4° C. overnight, as in the conventional methods. The concentration of the peptide solution used for immobilization may be appropriately selected depending on the type of the peptide, and type and concentration of the substance to be measured in the test sample. For example, it is about 1 ng/ml to 100 µg/ml.

After binding the peptide to the substrate, the functional groups of the side chains of the amino acids are deprotected. The methods for the deprotection are also well-known, and are described in, for example, Kiyoshi NOKIHARA, Journal of Synthetic Organic Chemistry Japan, 52, 347-358, 1994, "Highly Efficient Peptide Synthesis: Simultaneous and Automatic Synthesis of Multiple Peptides and Peptide Library"; Kiyoshi NOKIHARA and Yoshio YOKOMIZO, Shimadzu Review, 52, 1-8, 1995, "Cleaving Off of Synthetic Peptides by Fmoc-tBu Strategy"; Kiyoshi NOKIHARA, Rintaro YAMAMOTO, Hajime HAZAMA, Shin NAKAMURA, Shimadzu Review, 50, 33-43, 1993 "Development of Practical Simultaneous Multiple Solid Phase Peptide Synthesizer PSSM-8"; and K. Nokihara, R. Yamamoto, M. Hazama, O. Wakizawa, S. Nakamura, and M. Yamaguchi, Peptide Chemistry 1991, ed., A. Suzuki, Protein Research Foundation, Osaka, 203-208, 1992, "Development and Applications of a Novel and Practical Simultaneous Multiple Solid Phase Peptide Synthesizer"; Chan, W. C.; White, P. D. Fmoc Solid Phase Peptide Synthesis: A Practical Approach; Oxford University Press: New York, 2000; pp 41-76. In general, the methods for cleavage used in solid phase synthesis (the methods for cleaving peptides from a resin and for simultaneously deprotecting side chains) may be used as they are. Under the reaction conditions for carrying out the cleavage, the peptide immobilized on the substrate is not cleaved from the substrate.

In the peptide-immobilized substrate according to the present invention, it is preferred to immobilize a plurality of kinds of peptides on a single substrate at specified regions, respectively. By so doing, a plurality of target proteins may be measured simultaneously. The number of the kinds of the peptides is not restricted, and usually, it is preferred to immobilize 100 to 10,000 kinds, more preferably about 1000 to 3000 kinds of peptides on a single substrate. As the substrate, any substrate which can bind the chemically synthesized peptides may be employed without restriction, and glass substrates such as slide glass, may be employed as in the conventional DNA chips. Substrates having small recesses or grooves may be employed, and wells of microplates may also be used as the substrates. In cases where the wells of a microplate are used as the substrates, the inner wall of each well constitutes the peptide-immobilized substrate. In cases where the peptides are immobilized by physical adsorption, it is preferred to use wells of a microplate, or grooves or recesses formed in a chip such as slide glass as the substrate, so that the peptide solution may be poured. By using a recess as the substrate when the peptides are immobilized by physical adsorption, the measurement may be carried out without problem even if a portion of the peptides are eluted into the solution during the reaction with the target proteins.

The peptide-immobilized substrate according to the present invention may be used for measuring the target protein(s). The term "measuring" herein includes both detection and quantification.

The measurement of the target protein(s) may be carried out by adding a sample which may contain the target protein(s) onto the peptide-immobilized substrate, allowing the reaction, then washing the chip and measuring the signal. The reaction with the sample may be carried out, usually, at 4° C. to 40° C. for about 1 minute to 3 hours, preferably at room temperature for about 1 minute to 15 minutes, but the reaction conditions are not restricted thereto.

The sample is not restricted at all. Examples of the sample include homoginates of animal cells, plant cells, bacterial cells and viruses as well as fractions thereof; body fluids such as blood, serum, plasma, urine, saliva, tissue fluid and spinal fluid; and various foods and beverages, but the samples are not restricted thereto.

By using the peptide-immobilized substrate according to the present invention, the target protein(s) may be measured accurately and simply.

The peptide-immobilized substrate according to the present invention may be used not only for the measurement of the intended target protein(s), but also for the screening of unknown target protein(s). That is, the number of the types of the basal oligopeptides which can have the particular spatial structures are thought to be about 10. Based on these oligopeptides, when considering the combinations of the sizes, acidities, basicities, aromaticities, aliphaticities and so on, the number of the basal peptides are thought to be about 3000. Thus, after chemically synthesizing these 3000 kinds of peptides and preparing the peptide-immobilized substrate according to the present invention using the peptides, various proteins are reacted with the substrate. By so doing, what protein reacts with what peptide having what spatial structure may be examined. By accumulating the results to produce a database, a great number of proteins can be measured, which will largely contribute to the diagnoses of various diseases and developments of new drugs. Considering the diversity due to incorporation of non-naturally occurring amino acids, the number of the kinds of the oligopeptides exceeds 1,000,000. By virtue of these numerous peptides, the type of recognition may be classified in more detail, so that the accuracy of the diagnosis is thought to be promoted, when the substrate is applied to diagnosis.

By carrying out the method of the present invention on a plurality of chemically synthesized peptides, converting the measured value for each peptide into data with which differences between measured values may be recognized with naked eye, and outputting visible data of the peptides in an array, the protein(s) in the test sample may be measured easily and simply, and the protein(s) contained in an unknown sample may be identified or characterized.

Preferred examples of the data recognized with naked eye include, physical values related to color, such as color, brightness and/or chroma, and it is preferred that the difference in color can be recognized with naked eye depending on the measured value for each peptide. By this, the measured values can be distinguished with naked eye, and they are outputted in an array. By so doing, a colored pattern is formed by the measured values for the peptides. By increasing the number of the chemically synthesized peptides, this color pattern becomes unique to each test sample, so that it serves as if a fingerprint (the method according to the present invention in which the measured values are converted to data which can be recognized with naked eye may be referred to as "fingerprint method" for convenience).

Conversion of the differences among various values into visible data may easily be carried out by using a commercially available computer software. That is, data processing softwares which enable to make the differences among values be visible are commercially available. An example thereof is Igor Pro ver.4.04 (commercially available from WaveMetrics, Inc). By using such a data processing software, for example, by inputting the rate of change of the fluorescence intensities before and after the reaction with the immobilized chemically synthesized peptides as measured values into the software, it is possible to output colors such that, for example, the larger the rate of change, the more yellowish the color (this color can be selected in the software). Further, the colors corresponding to the measured values are outputted in an array. Therefore, a colored stripe pattern is formed for each test sample. Since this colored stripe pattern is unique depending on the type and amount of the protein contained in the test sample, it may be used as a fingerprint which enables to identify or characterize (judging of the characters or properties, identification or estimation of content) the protein contained in an unknown sample.

In this method, a plurality of target proteins may be contained in the test sample. Even when a plurality of target proteins are contained, since a unique colored pattern is outputted depending on the types and amounts of the target proteins, it can be used as a fingerprint of the sample. In this case, it is preferred that the chemically synthesized peptides which bind with each of the target proteins be immobilized on the substrate. However, even if there are no chemically synthesized peptides which bind with one or more of the plurality of target proteins, a colored stripe pattern is formed corresponding thereto, so that lack of the chemically synthesized peptides which bind to one or more target proteins is not necessarily problematic.

In the finger print method, those chemically synthesized peptides which have possibilities to bind with the target protein(s) (i.e., which also have possibilities not to bind with the target protein(s)) may also be immobilized on the substrate. For example, as described in the Examples below, chemically synthesized peptides each of which has a random region therein may be immobilized. In such a case, it is unknown what peptide binds with what target protein. However, anyway, since a unique colored pattern is outputted depending on the type(s) and amount(s) of the target protein(s), it can be used as a fingerprint of the sample.

By carrying out measurements by the fingerprint method using the same substrate on which chemically synthesized peptides are immobilized, accumulating the measured values to produce a database, and by comparing the measured data for an unknown sample with the measured data accumulated in the database, unknown test samples may be identified or characterized.

Since the fingerprint method is also one of the modes of the method according to the present invention using the above-described peptide-immobilized substrate, the above-described explanations about the chemically synthesized peptides, their labels, binding methods, test samples and reaction conditions are applicable to the fingerprint method.

EXAMPLES

The present invention will now be described in more detail by way of examples. It should be noted, however, that the present invention is not restricted to the examples below.

Example 1

Figure 3:
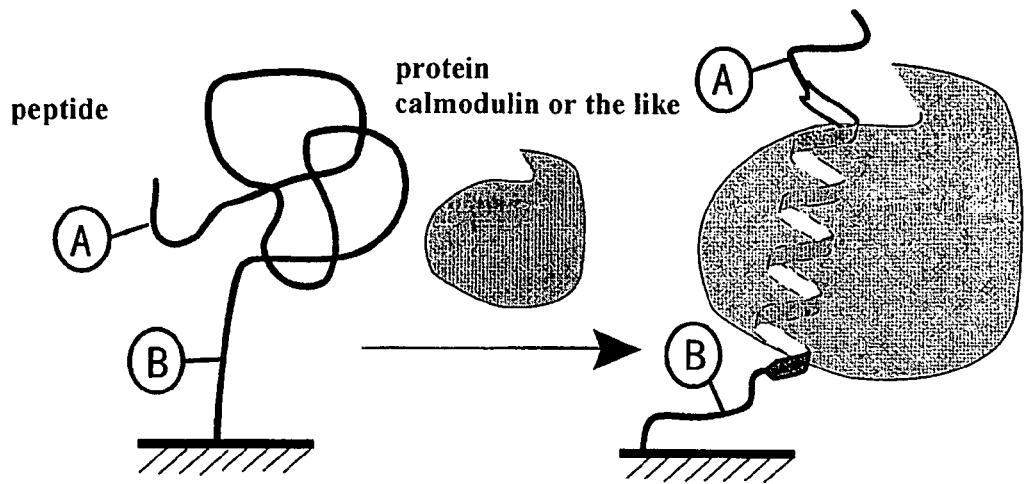
FIG. 3 schematically shows the measurement carried out in Example 1 of the present invention.

As schematically shown in FIG. 3, calmodulin was measured using a peptide chip in which peptides having α-helix structure, each of which both termini were labeled with different fluorescent labels, were immobilized on a substrate. The procedures were carried out as follows:

The sequence of the core region of the peptides, which forms α-helix structure was designed by molecular modeling using a computer (molecular modeling using Insight II/Discover, Molecular Simulation, U.S.) based on the amino acid sequence of the peptide described in a reference (K. T. O'Neil and W. F. DeGrado, Trend Biochem Sci, 15, 59-64 (1990)). As a result, the amino acid sequence Leu-Lys-Lys-Leu-Leu-Lys-Leu-Leu-Lys-Lys-Leu-Leu-Lys-Leu (SEQ ID NO:1) was employed as the amino acid sequence of the core region. To this sequence, a Cys residue as an anchor for immobilization, and Glu(Rf1), Lys(Rf2) and Lys(Rf3) as residues labeled with fluorescent labels were added to synthesize Cys-Glu(Rf1)-Leu-Lys-Lys-Leu-Leu-Lys-Leu-Leu-Lys-Lys-Leu-Leu-Lys-Leu-Lys(Rf2)-NH$_2$ (SEQ ID NO: 2), Glu(Rf1)-Leu-Lys-Lys-Leu-Leu-Lys-Leu-Leu-Lys-Lys-Leu-Leu-Lys-Leu-Lys(Rf2)-Cys-NH$_2$(SEQ ID NO: 3), and Lys(Rf3)-Leu-Lys-Lys-Leu-Leu-Lys-Leu-Leu-Lys-Lys-Leu-Leu-Lys-Leu-Cys-NH$_2$ (SEQ ID NO: Rf1, Rf2 and Rf3 were fluorescent groups, that is, ethyldansyl group, dabsyl group and carboxyfluorescein group, respectively. Fluorescent amino acid derivatives in which the fluorescent groups (A and B in FIG. 3) were introduced in the side chains of glutamic acid and lysine were synthesized, and used as building blocks. The carboxylic acid to which a dabsyl group was attached was converted into N-hydroxysuccinimide-activated ester derivative using diisopropylcarbidiimide. The amino group in the side chain of Fmoc-Lys-OH (Product #04-12-1042, Novabiochem, Switzerland) and the above-described activated ester were stirred overnight at room temperature in dimethylformamide according to a conventional method. Thereafter, the reaction mixture was concentrated and precipitated with ether to obtain Fmoc-Lys(Rf2)-OH labeled with a fluorescent label (B in FIG. 3). Yield: 80%. (Fmoc: fluorenylmethyloxycarbonyl). Further, fluorescent amino acid Fmoc-Glu(Rf1)-OH obtained by introducing a fluorescent group (A in FIG. 3, ethyldansyl group) into the side chain of the glutamic acid Fmoc-Glu-OBut (tert-butyl ester) (Product #04-12-1075, Novabiochem, Switzerland), was synthesized. That is, the carboxylic acid in the side chain of Fmoc-Glu-OBut and ethyldansyl were condensed by water-soluble carbodiimide in dioxane-water (3:1), and tert-butyl ester was removed by trifluoroacetic acid, thereby synthesizing Fmoc-glutamic ethyl dansyl. Yield: 60%. Further, carboxyfluorescein was converted to N-hydroxysuccinnimide-activated ester derivative using diisopropylcarbidiimide. The amino group in the side chain of Fmoc-Lys-OH (Product #04-12-1042, Novabiochem, Switzerland) and the above-described activated ester were stirred overnight at room temperature in dimethylformamide according to a conventional method. Thereafter, the reaction mixture was concentrated and precipitated with ether to obtain Fmoc-Lys(Rf3)-OH labeled with a fluorescent label. Yield: 85%.

Using these products as the building blocks, the peptides labeled with the labels A and B in the drawing were synthesized in amounts of 15 μmol, respectively, by the solid phase peptide synthesis according to the well-known Fmoc strategy. That is, using TentaGel SRAM, Product #S30-023 (Rink-amide resin with polyethylene glycol chain) of Rapp Polymere, Germany, as the solid carrier, Fmoc-amino acid derivatives were sequentially condensed. This was carried out using the method described in Japanese Patent No. 2007165 entitled Multiple Simultaneous Chemical Reaction Apparatus, and using the Multiple Simultaneous Peptide Synthesizer Model PSSM-8 commercially available from Shimadzu Corporation.

The substrate was obtained by bromoacetylation of an aminopropyl glass (Product No. 2550, Corning, U.S.). That is, bromoacetic acid was dissolved in dimethylformamide, and water-soluble carbodiimide (1.05 equivalents) was added thereto under stirring while cooling the mixture in ice. Twenty minutes later, an aminopropyl glass plate was immersed therein and the mixture was stirred by gently shaking the whole mixture at room temperature for 2 hours. Then the glass plate was removed and washed with 50% aqueous dimethylformamide solution and tetrahydrofuran, followed by drying in a desiccator under reduced pressure.

Each of the synthetic peptides (concentration: 0.1 to 10 μM) was immobilized by being reacted with the brom groups on the substrate at room temperature for 30 minutes. With the system in which the combination of ethyldansyl-dabsyl groups was employed, measurement of fluorescence was performed employing exciting wavelength of 340 nm and detection wavelength of 480 nm. By adding a calmodulin solution (Tris buffer pH7.4, 150 mM NaCl, 0.1 mM CaCl$_2$, calmodulin concentration: 1.0 μM), about five times increase of the fluorescence intensity was measured using a fluorescence plate reader. Thus, the protein was able to be detected and quantified. With the system using the peptide containing carboxylfluorescein, measurement of fluorescence was performed employing exciting wavelength of 490 nm and detection wavelength of 520 nm. In the presence of the protein, about ten times increase of the fluorescence intensity was measured, so that the protein was able to be detected and quantified. The calmodulin solution and the peptide chip were reacted at 25° C. for 5 minutes.

Example 2

Figure 4:
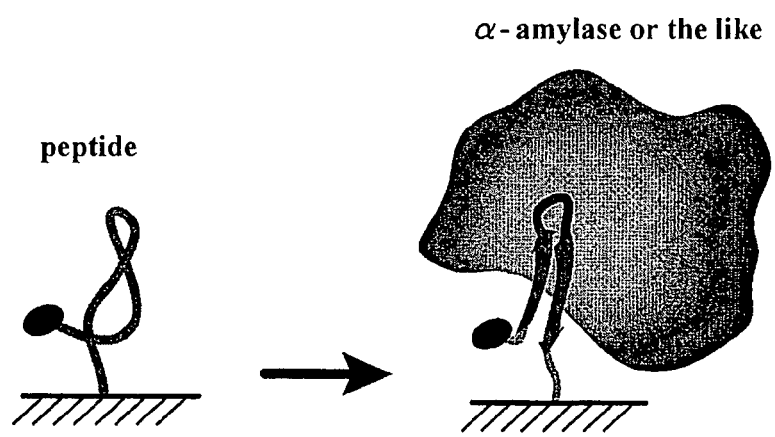
FIG. 4 schematically shows the measurement carried out in Example 2 of the present invention.

As schematically shown in FIG. 4, amylase was measured using a peptide chip in which a peptide whose one terminus was labeled with a fluorescent label, which peptide has β-loop structure, was immobilized on a substrate. The procedures were carried out as follows:

As in Example 1, as schematically shown in FIG. 4, a peptide which forms β-loop structure was designed by molecular modeling using a computer based on the amino acid sequence of the peptide described in a reference (F. J. Blanco et al., Eur J Biochem 200, 345-351 (1991), S. Ono et al, Biosci Biotechnol Biochem, 62, 1621-1623 (1998)). As a result, as the amino acid sequence of the core region, the sequence Tyr-Gln-Ser-Trp-Arg-Tyr-Ser-Gln-Ala (SEQ ID NO: 5) was employed. The peptide having this sequence to which Cys residue as an anchor for immobilization was added to one terminus, and to which Lys residue having a fluorescent group Rf (fluorescent group such as carboxyfluorescein in FIG. 4) was added to another terminus, was synthesized. Thus, the sequence was Lys(Rf)-Tyr-Gln-Ser-Trp-Arg-Tyr-Ser-Gln-Ala-Cys-NH$_2$ (SEQ ID NO: 6). As in Example 1, using the fluorescent amino acid derivative having a fluorescent group (such as carboxyfluorescein) on the side chain of the amino acid as a building block, the peptides were synthesized by the solid phase peptide synthesis method using the Fmoc strategy in an amount of about 15 μmol, respectively. Each peptide (concentration: 0.1 to 10 μM) in Tris buffer, pH8.0 was immobilized on the plate through thioether bond as in Example 1. When carboxyfluorescein group was used, fluorescence measurement was performed employing exciting wavelength of 490 nm and detection wavelength of 520 nm. By adding an amylase solution (Tris buffer pH7.4, 150 mM NaCl, amylase concentration: 1.0 μM), about ten times increase of the fluorescence intensity was measured, so that the amylase was able to be detected and quantified. The amylase solution and the peptide chip were reacted at 25° C. for 5 minutes.

Example 3

Fingerprint Method

By the method described in detail below, 126 kinds of peptides having the sequences Ac-Cys-Glu-Thr-Ile-Thr-Val-Xaa-Xaa-Xaa-Xaa-Lys-Thr-Tyr-Lys(F)-Lys-NH2 (SEQ ID NO: 7) (wherein "Ac" represents acetyl group and (F) represents a fluorescent label) were synthesized, and each one of the peptides was immobilized on one well in a microplate. Each of the peptides was reacted with 1) α-amylase, 2) bovine serum albumin (BSA), 3) β-glucosidase, 4) β-galactosidase, 5) lysozyme, 6) cellulase, 7) β-lactoglobulin, 8) defatted almond powder (protein mixture), 9) mixture of 1) to 7) or 10) cell lysate of *E. coli*, and the fluorescence intensities before and after the reaction were measured. The rate of change of the fluorescence intensities were inputted in Igor Pro ver.4.04 (commercially available from WaveMetrics, Inc), and the colors corresponding to the values (the higher the value, the more yellowish) were outputted in an array.

As a result, colored stripe patterns characteristic to each of the test samples were obtained. The peptide number was taken along the abscissa such that a lateral width per one peptide was 1.5 mm (therefore, the overall width covering all of the 126 peptides was 1.5×126=189 mm), and the longitudinal length for each peptide was about 5 mm, so that the entire area of the pattern was landscape rectangular. The region for each peptide (rectangle having a width of 1.5 mm and length of 5 mm) was painted with a color corresponding to the rate of change of the fluorescence intensity, and the regions for each peptide are adjacently arrayed, thereby entirely forming a colored stripe pattern.

The concrete amino acid sequences of the region represented by -Xaa-Xaa-Xaa-Xaa- in the above-described sequence are shown in Table 2 below (SEQ ID NOS: 8-133 respectively).

TABLE 2

| Peptide No. | Sequence | Peptide No. | Sequence | Peptide No. | Sequence | Peptide No. | Sequence |
|---|---|---|---|---|---|---|---|
| 1 | LHGE | 33 | YHRG | 65 | YWGP | 97 | GLRS |
| 2 | LPGE | 34 | RHWG | 66 | YLHP | 98 | GWRS |
| 3 | RPHE | 35 | SYWG | 67 | LRHP | 99 | REYS |
| 4 | YGLE | 36 | WEYG | 68 | HGLP | 100 | RLYS |
| 5 | WRLE | 37 | EHYG | 69 | LERP | 101 | GRYS |
| 6 | WYLE | 38 | ERYG | 70 | GLRP | 102 | HWYS |
| 7 | HGPE | 39 | LRYG | 71 | LYRP | 103 | GLEW |
| 8 | LHPE | 40 | ESYG | 72 | GESP | 104 | YHGW |
| 9 | HSPE | 41 | RGEH | 73 | ELSP | 105 | RLGW |
| 10 | YSPE | 42 | LYEH | 74 | ERSP | 106 | SLGW |
| 11 | YWPE | 43 | WRLH | 75 | LRSP | 107 | LEHW |
| 12 | LYPE | 44 | GWLH | 76 | GLYP | 108 | YRHW |
| 13 | LGSE | 45 | GRPH | 77 | SWYP | 109 | PSHW |
| 14 | WHSE | 46 | RSPH | 78 | PWER | 110 | EYHW |
| 15 | YHSE | 47 | LWPH | 79 | WEGR | 111 | YGLW |
| 16 | PWSE | 48 | LSRH | 80 | HLGR | 112 | EHRW |

TABLE 2-continued

| Peptide No. | Sequence | Peptide No. | Sequence | Peptide No. | Sequence | Peptide No. | Sequence |
|---|---|---|---|---|---|---|---|
| 17 | PHWE | 49 | LWSH | 81 | YHLR | 113 | PYRW |
| 18 | GPWE | 50 | LYSH | 82 | SGPR | 114 | LESW |
| 19 | PGYE | 51 | GEWH | 83 | WHPR | 115 | EYSW |
| 20 | RPYE | 52 | SGYH | 84 | WSPR | 116 | HPYW |
| 21 | SHEG | 53 | RYEL | 85 | WESR | 117 | RHEY |
| 22 | PREG | 54 | WPGL | 86 | HWSR | 118 | HPEY |
| 23 | WSEG | 55 | SGHL | 87 | SPYR | 119 | WLHY |
| 24 | SPHG | 56 | HSPL | 88 | GWYR | 120 | RPHY |
| 25 | WSHG | 57 | EHRL | 89 | GRES | 121 | SPHY |
| 26 | YSLG | 58 | HESL | 90 | PWGS | 122 | SRHY |
| 27 | WHPG | 59 | YPSL | 91 | PYGS | 123 | WSLY |
| 28 | YHPG | 60 | RWSL | 92 | RGHS | 124 | PWLY |
| 29 | WRPG | 61 | PEWL | 93 | WPLS | 125 | WERY |
| 30 | LSPG | 62 | PRWL | 94 | ERLS | 126 | RSWY |
| 31 | RYPG | 63 | GHYL | 95 | BYLS | | |
| 32 | LERG | 64 | RWYL | 96 | EHRS | | |

Detailed Procedures in Example 3
Reagents and Apparatuses

All chemicals and solvents were of reagent or HPLC grade, and used without further purification. Dimethylformamide (DMF) as a solvent for the peptide synthesis was treated with molecular sieve 0.4 nm for overnight. Fmoc protected amino acid derivatives were purchased from Watanabe Chemical Co., Novabiochem or Shimadzu Scientific Research Inc. Side chain protections were as follows:
acetamidomethyl (Acm) or triphenylmethyl (Trt) for Cys;
t-butyl (tBu) for Asp, Glu, Thr, Tyr, Ser; Trt for Asn, Gln, His;
t-butyloxycarbonyl (Boc) or 4-methyltrityl (Mtt) for Lys;
2,2,4,6,7-pentamethyldihydrobenzofuran-5-sulfonyl (Pbf) for Arg.

Peptides were synthesized by the solid-phase method by means of Fmoc chemistry.

HPLC was performed on a system composed of a Hitachi D7500 Chromato-Integrator, a L7400 UV-VIS Detector using a Wakosil 5C18 (4.6×150 mm) for analysis or a YMC ODS A323 (10×250 mm) for purification or on a Shimadzu LC2010C system using a Cadenza CD-C18 column (4.6×50 mm) with a linear gradient of acetonitrile/0.1% trifluoroacetic acid (TFA) at a flow rate of 1.0 mL min$^{-1}$.

MALDI-TOFMS was performed on a Shimadzu KOMPACT MALDI III mass spectrometer with 3,5-dimethoxy-4-hydroxycinnamic acid (SA) or α-cyano-4-hydroxycinnamic acid (CHCA) as a matrix. Amino acid analyses were carried out using a Wakopak WS-PTC column (4.0× 200 mm, Wako Pure Chemical Industries) after hydrolysis in 6 M HCl at 110° C. for 24 h in a sealed tube and labeling by phenyl isocyanate (PITC).

Synthesis of Peptides with 15-23 Sequence

Assembly of peptide chain: The peptides were assembled on NovaSyn TGR resin (Novabiochem, 0.15 mmol/g). Fmoc-Tyr(tBu)-Gln(Trt)-Ser(tBu)-Trp-Arg(Pbf)-Tyr(tBu)-Ser(tBu)-Gln(Trt)-Ala-Cys(Acm)-resin (SEQ ID NO: 134) (Fmoc(15-23)Acm-resin) and Fmoc-Tyr(tBu)-Gln(Trt)-Ser(tBu)-Trp-Arg(Pbf)-Tyr(tBu)-Ser(tBu)-Gln(Trt)-Ala-Cys(Trt)-resin (SEQ ID NO: 134) (Fmoc(15-23)Trt-resin) and Fmoc-Tyr(tBu)-Gln(Trt)-Ser(tBu)-Trp-Arg(Pbf)-Tyr(tBu)-Ser(tBu)-Gln(Trt)-Ala-Lys(Mtt)-resin (SEQ ID NO: 135) (Fmoc(15-23)Mtt-resin) were synthesized on an Advanced ChemTech Model 348 MPS peptide synthesizer. Fmoc-amino acids (6 eq.) (equivalent may be hereinafter referred to as "eq".), 2-(1H-benzotriazole-1-yl)-1,1,3,3-tetramethyluronium hexafluorophosphate (HBTU, 6 eq.), HOBt.H2O (6 eq.) and DIEA (12 eq.) in NMP were used for coupling of amino acids (for 30 min, twice), and 25% piperidine in NMP was used for Fmoc-removal. DMF was used as solvent for other procedure such as washing.

Peptides Labeled by a Fluorescein Moiety, F(15-23)Acm and F(15-23)SH:

Fmoc(15-23)Acm-resin or Fmoc(15-23)Trt-resin were treated with 20% (v/v) piperidine/NMP to remove a Fmoc group. Then, 5(6)-carboxyfluorescein (5(6)-FAM, Molecular probes, Inc.) was coupled to N-terminus of peptides using 5(6)-FAM (1.5 eq.), HBTU (1.5 eq.), HOBt.H2O (1.5 eq.) and DIEA (3 eq.) in DMF for 1.5 h (×2) or 2.5 h (×1). The resin and the protecting groups except Acm were removed by 1 h treatment of TFA/m-cresol/ethanedithiol/thioanisole (40/1/3/3, v/v) at room temperature. The peptides were purified by RP-HPLC and characterized by MALDI-TOFMS: F(15-23)Acm m/z 1721.4 ([M+H]+calcd. 1721.8); F(15-23)SH 1649.4 (1649.7).

Peptides Labeled by a Dansyl Moiety, D(15-23)Acm and D(15-23)SH:

Fmoc(15-23)Acm-resin or Fmoc(15-23)Trt-resin were treated with 20% (v/v) piperidine/NMP to remove a Fmoc group. A dansyl moiety was introduced to N-terminus of peptides using 5-dimethylaminonaphthalene-1-sulfonyl chloride (dansyl Cl, 3-6 eq.) in DMF for 2-3 h. The peptide was cleaved from resin and all protecting groups except Acm were removed according to the procedure same as fluorescein-labeled peptides. The peptides were purified by RP-HPLC and characterized by MALDI-TOFMS: D(15-23)Acm m/z 1596.3 ([M+H]$^+$ calcd. 1596.8); D(15-23)SH 1525.9 (1525.7).

Peptide Labeled by Fluorescein and EDANS Moieties, F(15-23)ED:

Fmoc(15-23)Trt-resin was treated with 20% (v/v) piperidine/NMP to remove a Fmoc group. A fluorescein moiety was introduced to N-terminus of peptides using 5(6)-carboxyfluorescein succinimisyl ester (5(6)-FAM, SE, Molecular probes, Inc., 1.2 eq.) and DIEA (2 eq.) in DMF for 7 h. The peptide was cleaved from resin and all protecting groups were removed according to the procedure same as fluorescein-labeled peptides and purified by RP-HPLC. The obtained peptide was dissolved in 100 mM Tris-HCl (pH 7.4) and N-(iodoacetaminoethyl)-1-naphthylamine-5'-sulfonic (IAEDANS, Research Organics, 3 eq.) dissolved in DMF was added. After 1 h, the reactant was purified by RP-HPLC. The peptide was characterized by MALDI-TOFMS: F(15-23)ED m/z 1959.2 ([M+H]$^+$ calcd. 1956.0).

Peptides Labeled by a Toumarin Moiety, H(15-23)C or Coumarin and Fluorescein Moieties, F(15-23)C:

Fmoc(15-23)Mtt-resin were washed by CHCl$_3$ (four times) and DCM (once) and then treated with DCM/TIS/TFA=94/5/1 (4-6 times for 2 min each) to remove a Mtt group. After washing the resin with CHCl$_3$ (five times) and NMP (five times), a coumarin moiety was introduced into the side chain amino group of Lys residue using 7-diethylaminocoumarin-3-carboxylilc acid (Fluka, 2 eq.), HBTU (2 eq.), HOBt.H2O (2 eq.) and DIEA (4 eq.) in NMP for 30 min (×2). Then, Fmoc group of peptide was removed by the treatment with 20% (v/v) piperidine/NMP and fluorescein moiety was introduced to the N-terminus of peptides by the procedure same as fluorescein-labeled peptides. The peptide was cleaved from resin and all protecting groups were removed according to the procedure same as described above. The peptides were purified by RP-HPLC and characterized by MALDI-TOFMS: H(15-23)C m/z 1559.7 ([M+H]$^+$ calcd. 1559.7); F(15-23)C 1919.3 (1918.0).

Synthesis of Peptides with Designed Loop Sequence

The peptides were assembled on Rink amide SS resin (Advanced ChemTech, 0.6 mmol/g). Fmoc-Cys(Trt)-Glu(OtBu)-Thr(tBu)-Ile-Thr(tBu)-Val-Ser(tBu)-Trp-Arg(Pbf)-Tyr(tBu)-Lys(Boc)-Thr(tBu)-Tyr(tBu)-Lys(Mtt)-Lys(Boc)-resin (SEQ ID NO: 136) (Fmoc-Loop1(Mtt)-resin) was synthesized on an Advanced ChemTech Model 348 MPS peptide synthesizer with the same procedure described above. Each peptide-resins were washed by CHCl$_3$ (four times) and DCM (once) and then treated with DCM/TIS/TFA=94/5/1 (4-6 times for 2 min each) to remove a Mtt group. After washing the resin with CHCl$_3$ (five times) and DMF (five times), 5(6)-FAM, SE was coupled into the side chain amino group of Lys residue using 5(6)-FAM, SE (3 eq.) and DIEA (1.5 eq.) overnight. The peptide was cleaved from resin and all protecting groups were removed according to the procedure as described above. The peptides were purified by RP-HPLC and characterized by MALDI-TOFMS: Loop1 m/z 2306.9 ([M+H]$^+$ calcd. 2306.6).

Fluorescence Spectroscopy

Fluorescence spectra were recorded on a Hitachi fluorescence spectrophotometer 850 with a thermo-regulator using a quartz cell with 10 mm pathlength. All measurements were performed at 25° C., in 20 mM Tris-HCl (pH 7.4) or 20 mM Tris-HCl containing 150 mM NaCl (pH 7.4).

Circular Dichroism Spectroscopy

Circular dichroism spectroscopy was performed on a Jasco J-720WI spectropolarimeter with thermo-regulator using a quartz cell with 1 mm pathlength. All the measurements were performed in 20 mM Tris-HCl containing 150 mM NaCl (pH 7.4) at 25° C.

Construction of Peptide Library

The designed libraries were synthesized on a module for multiple simultaneous synthesis SRM96 (Shimadzu Scientific Research Inc). The synthesis was carried out based on the instructions by the manufacturer and the following reference: Reference: Tadashi YASUHARA, Kiyoshi NOKIHARA, Tadasu FURUSHO and Eiko KATAOKA, Tokyo University of Agriculture, Nogaku Shuho (Journal of Tokyo University of Agriculture), 43, 260-267, 1999.

The peptide library consisting of 63 library peptides and the peptide with native sequence (SWRY) (SEQ ID NO: 137), that is, totally 64 kinds of peptides were synthesized at once.

The peptide chain were assembled on a 4-(2',4'-dimethoxyphenyl-Fmoc-aminomethyl)phenoxyacetamido-norleusyl-MBHA resin (Rink amide MBHA resin). The common residues sequence at the C-terminus were coupled assembled in bulk using a Big LibraTube Rt20 (Shimadzu Scientific Research Inc.). Then, the dried resin was dispensed into the reaction tube of a SRM96 and following residues were coupled on a SRM using HBTU (10 eq.), HOBt.H2O (10 eq.) and DIEA (12 eq.). Protected amino acid (10 eq.) was reacted as an acyl component. After assembly of all peptide chain, an Mtt group in the side chain (ε-position) of the protected peptide resin of interest was removed by the treatment with the solution of DCM/TIS/TFA=94/5/1 (for 20 min) and fluorescein moiety were introduced by using 5(6)-FAM (6 eq.) with HBTU (6 eq.), HOBt.H2O (6 eq.) and DIEA (9 eq.), or 5(6)-FAM (5 eq.) O-(7-azabenzotriazol-1-yl)-1,1,3,3-tetramethyluronium hexafluorophosphate (HATU, 5 eq.) and DIEA (6 eq.). The fact that the reaction was completed very specifically was proved by characterization of cleavaged peptides.

Peptide chains were liberated from the resin. This procedure is called cleavage in this field. For cleavage of peptides from resin and side chain deprotection, the mixture of TFA/m-cresol/ethaneditiol/thioanisole (40/1/3/3, v/v) was used as a cleavage cocktail. For 64 peptides, ca. 20 mL of solution was prepared. To collect the filtrates, a 96-well glass titerplate was equipped under a tube holder. The cleavage cocktail was added to the resins in reaction tubes dropwise over 30 min, and leave for 1 h. Then resins were washed with small amount of cleavage cocktail. The filtrates containing peptides were concentrated by N$_2$ blowing, and then diethyl ether was added to precipitate the peptides. The solution with precipitants were transferred into 1.5 mL polypropylene tube, and centrifuged to collect precipitants. The precipitant were washed with fresh ether for 5 times and dried in centrifugal evaporator.

The crude peptides were purified by gel permeation chromatography (GPC) using SRM96, of which tubes were filled with Sephadex G-10 (Pharmacia) swelled with 10% (v/v) AcOH aq. (ca. 100 μL per tube). Since the peptides labeled with the fluorescent label were colored, the desired fraction was easily obtained by visual observation. The solution was evaporated to dryness by centrifuging evaporator. The residual acetic acid was removed by freeze drying with addition of water. The resulted peptides were dissolved in 200 μL of MeOH and stored with tightly capped at 4° C.

Absorption Measurements in 96-Well Plate

In order to estimate the concentrations of the above stock solutions of peptides, absorbance at 490 nm of the solutions of prepared peptides were measured by using Benchmark Multiplate Reader (Bio-Rad Laboratories) with 490 nm filter using microtiter plate (Assay Plate, Asahi Techno Glass). Stock solutions (in MeOH) of peptides were diluted by 20 mM Tris-HCl containing 150 mM NaCl (pH 7.4). The concentrations of stock solutions were estimated by the comparison of absorbance of each peptide to that of a standard peptide, whose peptide contents was determined by amino acid analysis.

Fluorescence Measurements in 96-Well Plate

Fluorescence intensities of the fluorescent-labeled peptides in microtiter plates (Assay Plate, Asahi Techno Glass) as solutions or immobilized to the substrates were measured on a PerSeptive Biosystems CytoFluor™ 4000TR multi-well plate reader at 30° C. Excitation and emission filters used were 485/20 and 530/10 (for fluorescein-labeled peptides), 360/20 and 515/10 (for a dansyl-labeled peptide), 450/50 and 530/10 (for a coumarin and fluorescein labeled peptide), respectively.

Peptide Immobilization to 96-Well Polystyrene Plates

Synthesis of Tresyl Activated Dextran (TAD):

Dextran (100.0 mg, average MW 64,000-76,000, Sigma D4751) was freeze dried from water (ca. 20 mL). Dried dextran was dissolved in hexamethylphosphoric triamide (10 mL) at 115° C. in a 50 mL single necked round bottom flask connected with a calcium chloride tube. The solution was brought to room temperature, and 2,2,2-trifluoroethanesulfonyl chloride (tresyl chloride, 220 μL, 2 mmol, Aldrich 32,478-7) were added dropwise over 1 min under magnetic stirring. After 15 min, dry pyridine (440 μL, 5.4 mmol) was added dropwise over 1 min. The product was precipitated from cold ethanol (ca. 20 mL). The peptide was collected by centrifugation and washed twice with fresh ethanol twice. Finally the product was dissolved in aqueous acetic acid (1% v/v in water, ca 10 mL), freeze dried and stored at −20° C. Yield; 120.2 mg. This yield corresponded to 7.4% of the hydroxyl groups in the dextran molecule (one out of 4.5 glucose units) were tresylated and this result was agreeable with the results described in the reference. Reference: K. Gregorius, S. Mouritsen, H. I. Elsner, J. Immunol. Meth., 1995, 181, 65-73.

Preparation of BrAc Modified Microtiter Plates:

A solution of poly-L-lysine (MW 70,000-150,000, Sigma P1274, 0.01 mg/mL) in carbonate buffer (0.1 M, pH 9.6) was added into each well of to polystyrene microtiter plates (Assay Plate, Asahi Techno Glass, 150 μL per well) and the plates were incubated for 2 h at room temperature or overnight at 4° C. The poly-L-lysine coated plates were washed four times with washing buffer (10 mM phosphate, 2.7 mM KCl, 500 mM NaCl, 1% (v/v) Triton X-100, pH 7.2), three times with water, and dried with $N_2$. Then, the above TAD (supra) (0.5 mg/mL) in phosphate buffer (10 mM phosphate, 150 mM NaCl, pH 7.2) was added to the poly-L-lysine coated plates (150 L/well) and incubated for 2 h at 4° C. After washing with water and drying, 1,4-diaminobutane (10 mM, diluted from 1 M stock solution in DMF) in the carbonate buffer was added to the TAD modified plates (100 μL/well) and incubated for 2 h at room temperature. Following a wash by water, blocking solution (0.1 M 2-aminoethanol in water, pH 8.0 adjusted by HCl) was added (200 μL/well) and incubated for 2 h at room temperature. The amino-functionalized plates were then washed three times with the washing buffer (supra), three times with water, and dried with $N_2$.

Bromoacetic acid was introduced to the amino-functionalized plates using its anhydride. Bromoacetic acid anhydride was prepared in situ by mixing of BrAcOH (0.6 M) and DIC (0.3 M) in DMF or NMP for 60 min. It was diluted to 10 mM by water and added to the plate (100 μL/well), and incubated for 5 h at room temperature or overnight at 4° C. The plates were washed three times with water, and further processed as below.

Preparation of Peptide-Bound Microtiter Plates:

The peptides with free SH group were dissolved in MeOH as stock solutions (ca. 1 mM). The peptides solution were diluted to 10 μM by 100 mM Tris buffer (pH 8.0) and immediately added to the bromoacetylated acid-modified plate (100 μL/well). The plate was incubated for 10 h at room temperature and then washing with the washing buffer for overnight at 4° C. After washing with water and dried with $N_2$, the plate was kept at 4° C.

Protein Detection Assay by Using Immobilized Peptides

All measurements were performed in 20 mM Tris-HCl containing 150 mM NaCl (pH 7.4). Purified and partially purified proteins were purchased from Sigma-Aldrich Japan (1. α-amylase from *Aspergillus oryzae*: A6211, 2. albumin from Bovine serum (BSA): A6793, 3. β-glucosidase from Almonds: G0395, 4. β-galactosidase from *Aspergillus oryzae*: G5160, 5. lysozyme from Chicken egg white: L6876, 6. cellulase from *Aspergillus niger*: C1184, 7. β-lactoglobulin from Bovine milk: L3908, 8. almond meal (protein mixture): A3265). Additionally, cell lysate of of *E. coli*, was also used.

The solutions of proteins (0.5 mg/mL) were added to the peptide-immobilized plate (100 μL/well), and the plate was incubated at 4° C. for 24 hours. The fluorescence intensities (1) were measured by using a microplate reader (CytoFluor™) at 30° C. After washing with water, the buffer was added to the plates (100 μL/well) and measured fluorescence intensities ($I_0$) again by using a microplate reader (CytoFluor™) at 30° C. The experiments were repeated twice for each protein and the averages of $I/I_0$ were recorded.

Preparation of *E. coli* Cell Lysate

*E. coli*. JA221 (F-, hsdR, DtrpES, leuB6, lacY, recAI) was inoculated onto ca. 5 mL of liquid media composed of 1% trypton, 0.5% yeast extract, and 1% NaCl (w/v) and preincubated at 37° C. for overnight. Then all of the culture was inoculated into 400 mL of same media and incubated at 37° C. for overnight with vigorous shaking. The cells were harvested by spinning, and the cell pellets were suspended in the buffer (100 mM potassium phosphate, pH 6.5), followed by washing. The washed cells were resuspended in 16 mL of the buffer and disrupted by sonication using ultrasonic disintegrator in an ice bath. Cell debris and larger particles were removed by centrifugation at 12000 rpm for 20 min, and the supernatant was collected. Total protein concentration of obtained supernatant was estimated as 30 mg/mL, by using Bio-Rad DC Protein Assay kit. The solution was diluted to a concentration of 0.86 mg/mL with 1.0 mM of phenylmethylsulfonyl fluoride and 5 mM of EDTA, and analyzed by the peptide-immobilized plate.

Processing by Computer of Fingerprint-Like Fluorescence Data

The fluorescence data for each protein, obtained by the peptide library immobilized on the plate, were converted into a graph like a fingerprint. As an example, the case carried out by using a software Igor Pro ver.4.04 (WaveMetrics, Inc.) will now be described. First, the peptides (1-126) were taken along the x-axis. The line of y=1 was displayed as a line graph for all proteins (10 lines) (1. α-amylase from *Aspergillus oryzae*, 2. albumin from Bovine serum (BSA), 3. β-glucosidase from Almonds, 4. β-galactosidase from *Aspergillus oryzae*, 5. lysozyme from Chicken egg white, 6. cellulase from *Aspergillus niger*, 7. β-lactoglobulin from Bovine milk, 8. almond meal (protein mixture), 9. mixture of 1-7, 10. *E.* coli soluble proteins (cell homogenate)). Then these lines were displayed after shifting the y-axis, and the fluorescence response value ($I/I_0$) for each protein was assigned to each line as the value of z-axis. As the color gradation, yellow-hot was selected from the patterns included in the software. As a result, characteristic fluorescence response pattern (protein fingerprint) depending on the amino acid sequences of the peptides was obtained for each protein, and the proteins were able to be characterized from the patterns with high reproducibility.

The invention claimed is:

1. A method for measuring one or more target proteins in a test sample, comprising the steps of:
bringing a plurality of chemically synthesized peptides each having 3 to 50 amino acids, each of which has an expected spatial structure and at least one of said chemically synthesized peptides is capable of binding with said target protein, into contact with said test sample which may contain the target protein;
100 to 10,000 types of said chemically synthesized peptides are immobilized on the same or different substrate,
each of said plurality of chemically synthesized peptides being labeled with at least one label wherein a signal is changed upon binding of said labeled chemically synthesized peptide with a target protein;
measuring the change of said signal due to target protein binding said labeled chemically synthesized peptides;
assigning a different color or a different brightness or chroma of a single color to an increment of change in signal, wherein the differences in assigned color, brightness or chroma can be distinguished by the naked eye; and
converting the measured values in the change of said signal for each labeled chemically synthesized peptide into a visible array displaying the different color or the different brightness or chroma of a single color for each labeled chemically synthesized peptide based on the measured change of signal for said labeled chemically synthesized peptide, wherein differences between measured values for different labeled chemically synthesized peptides can may be recognized with a naked eye in the visible array, thereby creating a unique visual pattern characteristic of the test sample.

2. A method for identifying or characterizing one or more proteins in a test sample comprising:
carrying out the method according to claim 1 for various samples containing one or more identified or characterized proteins;
accumulating outputted measured values to produce a database;
comparing a visible array of measured data for an unknown test sample containing said one or more unidentified or uncharacterized proteins with the visible arrays of measured data in said database thereby identifying or characterizing said unknown test sample.

3. The method according to claim 1, wherein at least a portion of said plurality of peptides contain random sequences in at least a part of their amino acid sequences.

4. The method according to claim 1, wherein at least a portion of said plurality of chemically synthesized peptides have amino acid sequences which are so molecularly designed as to attain said expected spatial structure.

5. The method according to claim 1, wherein each of said labels is a fluorescent label bound to an amino acid located at a particular site, which amino acid is one of the amino acids constituting said peptide.

6. The method according to claim 5, wherein two types of fluorescent labels are bound to particular amino acids located at different sites in a single peptide.

7. The method according to claim 6, wherein said labels are bound to one or both termini of said single peptide.

8. The method according to claim 1, wherein each of said chemically synthesized peptides is one synthesized while protecting functional groups in the side chains of the amino acids, and is bound to said substrate at a desired site by binding the peptide to the substrate while protecting said functional groups which are then deprotected after said peptide is bound to said substrate.

9. The method according to claim 1, wherein each of said chemically synthesized peptides has at least one functional group at its terminus, which chemically binds to said substrate, and is bound to said substrate via said functional group.

10. The method according to claim 9, wherein each of said chemically synthesized peptides has cysteine at one terminus thereof, and is bound to said substrate through the sulfhydryl group of said cysteine.

11. The method according to claim 1, wherein said plurality of chemically synthesized peptides are bound to said substrate by a covalent bond.

12. The method according to claim 1, wherein each of at least a portion of said plurality of chemically synthesized peptides has a core region for binding with said target protein, wherein the core region also has at least one label attached thereto and said core region having a spatial structure for optimal binding with said target protein.

13. The method according to claim 1, wherein the spatial structure of the peptide is selected from the group consisting of an α-helix, α-loop-α, β-turn, β-loop-β and a β-strand.

14. A method for identifying or characterizing one or more proteins in a test sample comprising:
carrying out the method according to claim 1 for various samples containing one or more identified or characterized proteins;
comparing a visible array of measured data for an unknown test sample containing one or more unidentified or uncharacterized proteins with the visible array(s) of measured data of the one or more identified or characterized proteins.

* * * * *